United States Patent
Oldham et al.

(10) Patent No.: US 10,617,892 B2
(45) Date of Patent: Apr. 14, 2020

(54) METHODS FOR GENERATING ACCURATE RADIATION DOSE MAPS CORRECTED FOR TEMPORAL AND SPATIAL CHANGES ARISING IN REMOTE DOSIMETRY APPLICATIONS

(71) Applicant: Duke University, Durham, NC (US)

(72) Inventors: Mark Oldham, Durham, NC (US); Stewart Biedeman Mein, IV, Durham, NC (US)

(73) Assignee: Duke University, Durham, NC (US)

( * ) Notice: Subject to any disclaimer, the term of this patent is extended or adjusted under 35 U.S.C. 154(b) by 195 days.

(21) Appl. No.: 15/941,199

(22) Filed: Mar. 30, 2018

(65) Prior Publication Data

US 2018/0280731 A1 Oct. 4, 2018

Related U.S. Application Data

(60) Provisional application No. 62/478,693, filed on Mar. 30, 2017.

(51) Int. Cl.
*A61N 5/10* (2006.01)
*A61B 6/00* (2006.01)

(52) U.S. Cl.
CPC .......... *A61N 5/1075* (2013.01); *A61N 5/103* (2013.01); *A61N 5/1071* (2013.01); *A61B 6/542* (2013.01); *A61B 6/58* (2013.01)

(58) Field of Classification Search
CPC .......... A61B 6/547; A61B 6/542; A61B 6/58; A61N 5/1077; A61N 2005/1072; A61N 5/1075; A61N 5/1038
See application file for complete search history.

(56) References Cited

U.S. PATENT DOCUMENTS

2013/0218001 A1* 8/2013 Uhlemann ............. A61B 5/055 600/411

* cited by examiner

*Primary Examiner* — David P Porta
*Assistant Examiner* — Fani Boosalis
(74) *Attorney, Agent, or Firm* — Quarles & Brady LLP (57) ABSTRACT

A method for generating a radiation dose map of a dosimeter indicating a spatial distribution of radiation dose imparted to the dosimeter. The corrected radiation dose map may be generated with the computer system by applying temporal correction factor and spatial correction factors to a measured radiation dose map, the corrected radiation dose map having pixel values associated with the measured radiation dose having been corrected for temporal effects caused by changes in the measure of radiation dose imparted to the dosimeter between the first time point and the second time point, and for spatial effects caused by the sensitivity of the dosimeter to radiation measurements as a function of the spatial dimension.

20 Claims, 4 Drawing Sheets

METHODS FOR GENERATING ACCURATE RADIATION DOSE MAPS CORRECTED FOR TEMPORAL AND SPATIAL CHANGES ARISING IN REMOTE DOSIMETRY APPLICATIONS

CROSS-REFERENCE TO RELATED APPLICATIONS

This application claims the benefit of U.S. Provisional Patent Application Ser. No. 62/478,693, filed on Mar. 30, 2017, and entitled "SYSTEMS AND METHODS FOR MRI-GUIDED RADIATION THERAPY."

BACKGROUND

Decades after the introduction of intensity modulated radiotherapy to the clinic, precise dosimetric commissioning of complex radiotherapy treatments remains a clinical challenge. With the advent of commercially available magnetic resonance imaging guided radiotherapy (MR-IGRT) systems, the permanent magnetic field introduces yet another source of uncertainty in the prediction of dose distributions—an already error-prone process.

Image guidance in high-precision radiotherapy affords the ability to frequently image during a treatment to improve accuracy of the dose delivery (i.e. gating, adaptive planning). In conjunction with delivery systems (such as a linear accelerator for photons and electrons, or cyclotron for protons), magnetic resonance imaging (MRI), computed tomography (CT) and x-ray imaging help visualize anatomical structures prior to or during treatment, especially movement-prone regions (i.e. lungs, liver and prostate). As the complexity of these devices increases so do the clinical needs to maintain a high-standard of care. The MRIdian® (by ViewRay) is a novel example of cutting-edge MR-IGRT technology which could benefit from true multi-dimensional dose validation.

ViewRay's MRIdian® system affords real-time MR image guidance during treatment, with enhanced soft-tissue contrast over on-board CT at no additional dose of radiation to the patient. However, the presence of an MR-field for on-board imaging in radiotherapy introduces clinical hurdles. Two examples include (1) asymmetry of the point spread kernel in homogeneous tissue, leading to reduced build-up and asymmetric penumbra, and (2) the electron return effect (ERE), which occurs at the boundaries between tissue and air.

To combat these hurdles, recent studies have tested the feasibility of in-situ 3D dosimetry with three different gels (BANG, MAGIC and Fricke) on the ViewRay. Similar works provide a dosimetry program for ViewRay's patient-specific IMRT QA, which include one-dimensional multi-point ionization chamber measurement, two-dimensional (2D) radiographic film measurement using a 30×30×20 cm phantom with multiple inserted ionization chambers, quasi-three-dimensional diode array (ArcCHECK) measurement with a centrally inserted ionization chamber, 2D fluence verification using machine delivery log files, and 3D Monte-Carlo Simulation.

In 2013, Juang, et al., investigated the feasibility of remote high-resolution 3D dosimetry with the PRESAGE®/Optical-CT system. Measured on-site (t=1 hr) and remote (t=48 hr) scans were taken of simple 4-field box deliveries and served as the reference distribution for 3D gamma analysis. Both on-site and remote measurements agreed well with TPS dose, with passing rates of 97.4%±2.2% and 97.6%±0.6%, respectively, for 3%/3 mm, criteria 10% dose threshold. However, some discrepancies were observed, for which corrections would need to be derived to achieve clinical grade dosimetry. In this study, changes in optical density between on-site and remote scanning in small volume dosimeters were observed.

In other past studies, volume and temporal effects have been noted where sensitivity and response differs over time and throughout the dosimeter. Thus, there remains a need to provide a comprehensive method that corrects for these effects.

SUMMARY OF THE DISCLOSURE

The present disclosure addresses the aforementioned drawbacks by providing a novel method for generating a corrected radiation dose map of a dosimeter indicating a spatial distribution of radiation dose imparted to the dosimeter. The method is capable of validation of advanced radiation treatments (e.g. MR-IGRT) through the use of one or more correction factors. These corrections factors may account for temporal and spatially-dependent behaviors observed within the dosimeter between irradiation and readout.

In one aspect, the present disclosure provides a method for generating a radiation dose map of a dosimeter indicating a spatial distribution of radiation dose imparted to the dosimeter. The steps of the method can comprise providing to a computer system, a radiation dose map obtained by measuring radiation dose imparted to a dosimeter after the dosimeter was exposed to radiation; providing to the computer system, a temporal correction factor that indicates a change in a measure of radiation dose imparted to the dosimeter between a first time point when the dosimeter was exposed to the radiation and a second time point when the radiation dose map was obtained; providing to the computer system, a spatial correction factor that indicates a sensitivity of the dosimeter to radiation measurements as a function of a spatial dimension; and generating a corrected radiation dose map with the computer system by applying the temporal correction factor and the spatial correction factor to the radiation dose map, the corrected radiation dose map having pixel values associated with the measured radiation dose having been corrected for temporal effects caused by changes in the measure of radiation dose imparted to the dosimeter between the first time point and the second time point, and for spatial effects caused by the sensitivity of the dosimeter to radiation measurements as a function of the spatial dimension.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for implementing a remote radiation dosimetry protocol that accounts for temporal changes in the properties of the dosimeter, as well as spatial sensitivity of the dosimeter. In general, a corrected radiation dose map is generated by measuring a radiation dose map and applying a temporal correction factor, spatial correction factor, or both, to the measured radiation dose map to correct for temporal effects, spatial effects, or both.

The methods described in the present disclosure provide for an improvement in the radiation dosimetry arts by offering improved accuracy and reliability in remote dosimetry protocols. For instance, the methods can improve the commissioning and quality assurance protocols for treatment sites that do not have specialized equipment or personnel for carrying out these processes. As such, the methods described in the present disclosure allow for the adoption of more specialized radiation treatment systems at more sites because the commissioning and quality assurance of those systems can be carried using the remote dosimetry protocols implemented with the methods described in the present disclosure.

In remote dosimetry processes, dosimeters are often shipped out from a first location, such as a central base institution, to a second location, such as a remote site, for irradiation, then shipped back to the first location for scanning and analysis. In some instances, the dosimeter may be sent to a different, third location, for scanning and analysis. The remote dosimetry processes can provide a convenient treatment validation service to institutions lacking the specialized equipment, resources, and manpower necessary to provide robust dosimetry. The remote site may be at a different geographical location than the central base institution or it may be located in a different area of the central base institution. For example, the remote site may be a different room within the central base institution.

Figure 1:
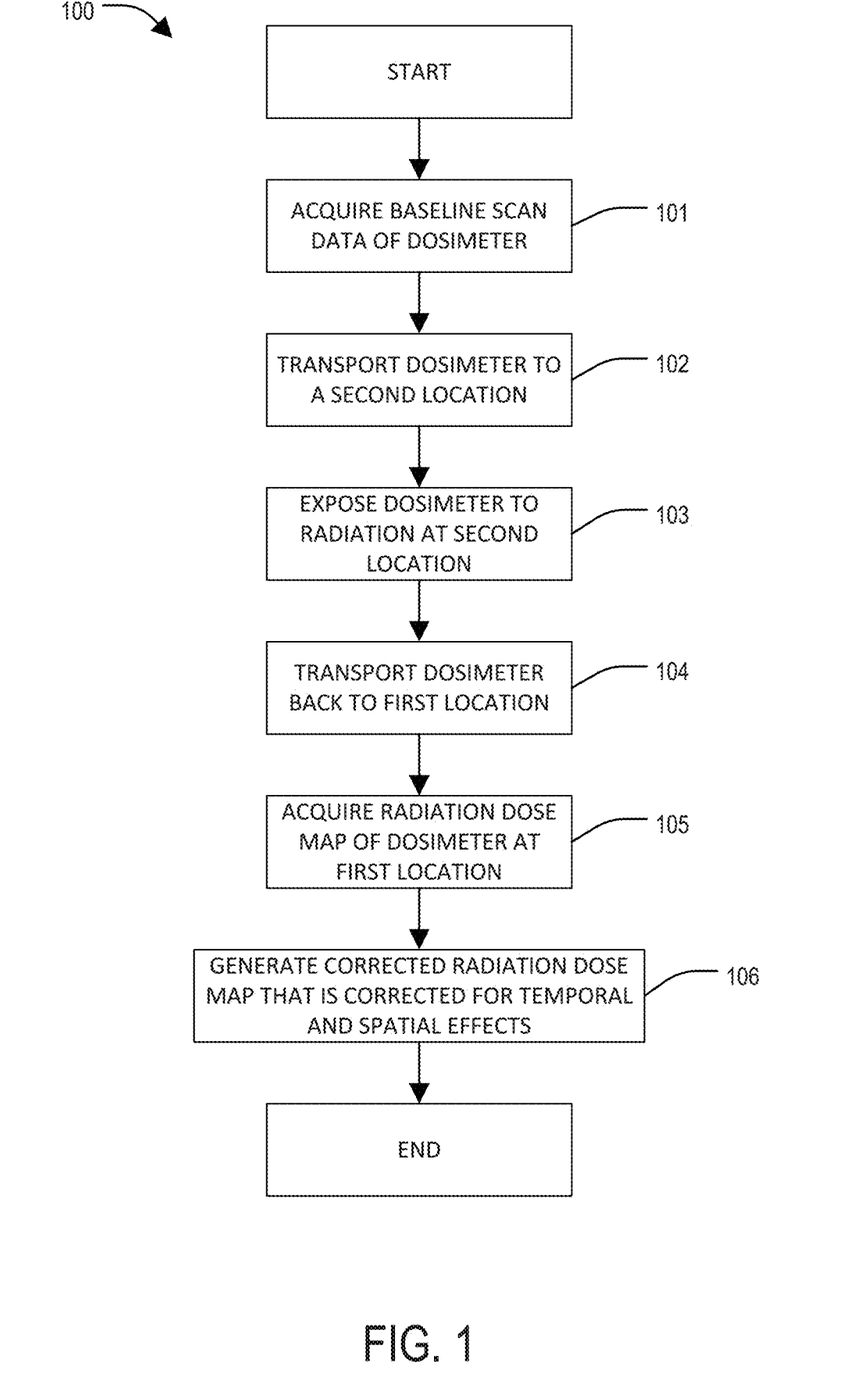
FIG. 1 depicts a process flowchart for a remote dosimetry process in accordance with the teachings of the present disclosure.

FIG. 1 depicts a flowchart 100 for an example remote dosimetry process. The process generally includes acquiring baseline scan data associated with a dosimeter at a first location 101. The dosimeter used to acquire and provide the baseline scan data may be the same dosimeter that is used to obtain the radiation dose map. Alternatively, the baseline scan data may be acquired and provided from a different dosimeter with similar radiation sensitivity characteristics. The dosimeter is then transported to a second location 102 where it is exposed to radiation 103. The dosimeter is then transported back to the first location 104, where a radiation dose map of the dosimeter is acquired 105. A corrected radiation dose map that has been corrected for temporal and spatial effects is then generated 106. Methods used to generate the corrected dose map in process block 106 are provided for in the present disclosure. Remote dosimetry methods are capable of validating advanced radiation treatments through the use of one or more correction factors for temporal and spatial effects. Such temporal effects can include changes in the characteristics of the dosimeter as a function of time from when the dosimeter was irradiated. As one example, the change in the dosimeter characteristics can include changes in the radiochromic properties of the dosimeter. Spatial effects that can be corrected for include the spatial sensitivity of the dosimeter. In order to accomplish these functions, the methods of the present disclosure may rely on data obtained in process blocks 101-105 as well as other information acquired for the remote dosimetry components or the dosimeter itself.

The temporal effects noted above can include changes in the properties or characteristics of the dosimeter between a first time point and a second time point. A first time point may occur when the dosimeter is exposed to radiation 103. A second time point may occur when the radiation dose map is acquired from the dosimeter 105. Due to the unstable nature of certain dosimeters, any radiation dose map acquired after a period of time following irradiation may contain inaccuracies that need to be corrected. For example, if the second time point occurs several days after the first time point (as may be common in remote dosimetry protocols), the measured radiation dose map may significantly differ from one that is measured immediately. Further, spatial regions of varying radiosensitivity may be present within the dosimeters as a result of manufacturing processes and other variables. These temporal and spatial inaccuracies can reduce the quality of the radiation treatment validation and may eventually lead to inexact treatment of patients. The methods of the present disclosure can be used to generate a corrected radiation dose map with a computer system by applying a temporal correction factor and a spatial correction factor to the radiation dose map.

Figure 2:
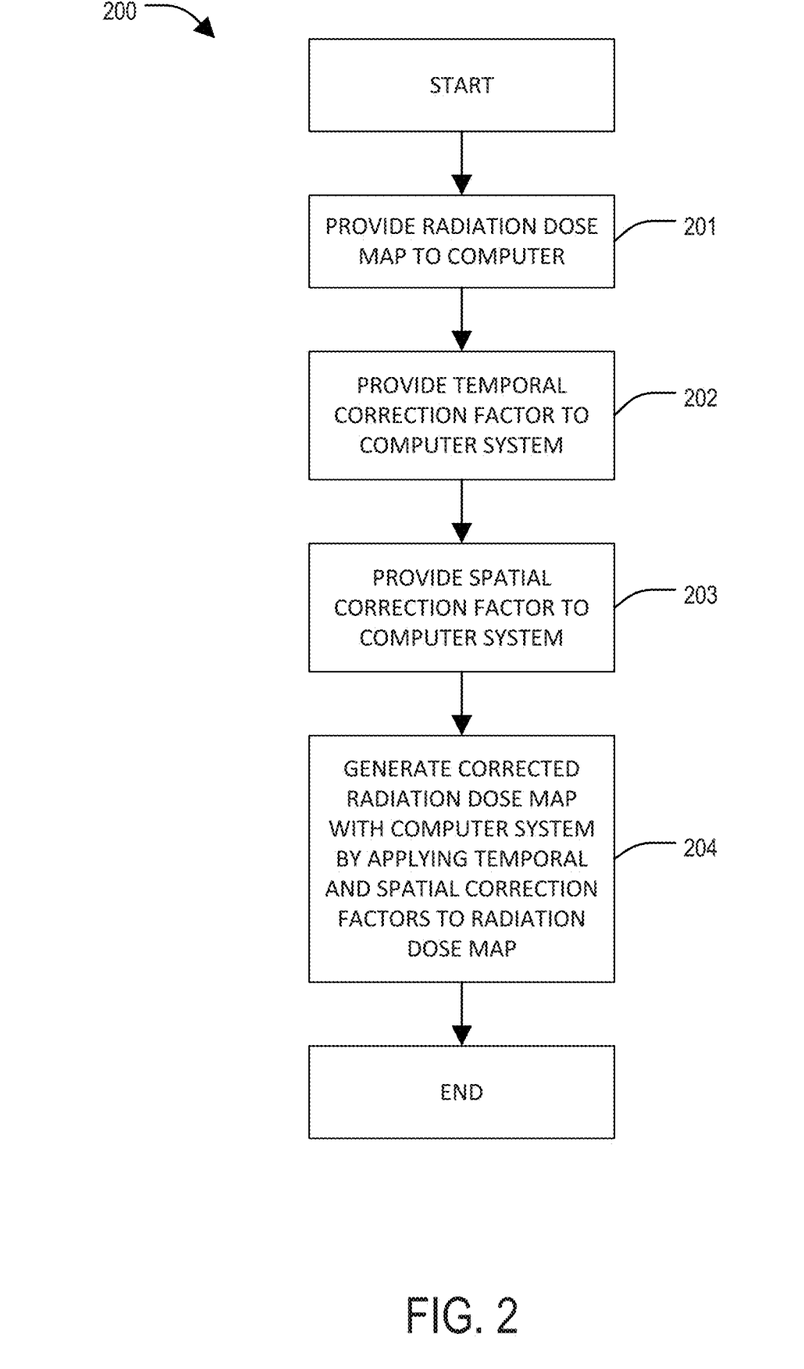
FIG. 2 depicts a method flowchart for generating a corrected radiation dose map of a dosimeter in accordance with the teachings of the present disclosure.

FIG. 2 depicts a method flowchart 200 for generating a radiation dose map of a dosimeter indicating a spatial distribution of radiation dose imparted to the dosimeter. The method includes providing to a computer system, a radiation dose map obtained by measuring radiation dose imparted to a dosimeter after the dosimeter was exposed to radiation 201. The radiation dose map can be provided to the computer system by retrieving a previously acquired radiation dose map from a memory or other storage device, or by acquiring a radiation dose map with a suitable measurement system that then communicates the radiation dose map to the computer system. As one example, the measurement system can be an optical computed tomography system.

A temporal correction factor is provided to the computer system 202. The temporal correction factor indicates a change in a measure of radiation dose imparted to the dosimeter between a first time point when the dosimeter was exposed to the radiation and a second time point when the radiation dose map was obtained. The temporal correction factor can be provided to the computer system by retrieving a previously calculated temporal correction factor from a memory or other data storage, or by calculating the temporal correction factor as needed. Example methods for computing a temporal correction factor are described below.

A spatial correction factor can also be provided to the computer system 203. The spatial correction factor indicates a sensitivity of the dosimeter to radiation measurements as a function of a spatial dimension. The spatial correction factor can be provided to the computer system by retrieving a previously calculated spatial correction factor from a memory or other data storage, or by calculating the spatial correction factor as needed. Example methods for computing a spatial correction factor are described below.

A corrected radiation dose map is then generated with the computer system by applying the temporal correction factor and the spatial correction factor to the measured radiation dose map 204. The corrected radiation dose map will include pixel, or voxel, values associated with the measured radiation dose having been corrected for temporal effects caused by changes in the measure of radiation dose imparted to the dosimeter between the first time point and the second time point, and for spatial effects caused by the sensitivity of the dosimeter to radiation measurements as a function of the spatial dimension.

The dosimeter used in the method of the present disclosure may advantageously be a three dimensional (3D) dosimeter. The dosimeter may be composed of a polymer. The dosimeter may be cylindrical, or any other suitable geometry. The dosimeter may be a radiochromic dosimeter. If such a radiochromic dosimeter is used, the computed temporal correction factor may indicate a change in an optical characteristic of the dosimeter between the first time point and the second time point. This optical characteristic may be coloration, optical density, or other such optical characteristics that are affected by radiation imparted to the dosimeter. The dosimeter may be composed of an optically transparent material.

One example of a dosimeter that may be used in the method of the present disclosure is the PRESAGE® (Heuris Inc.; Skillman, N.J.) 3D dosimeter. The PRESAGE® dosimeter is a radiochromic plastic dosimeter comprising a polyurethane matrix doped with LMG leuco dye. Prior to coming in contact with an activated free-radical initiator, LMG is a transparent chemical. When exposed to high-energy photons, LMG becomes oxidized and transitions to a colored (e.g., green) state. This color intensity change can be linearly correlated to a relative or absolute dose measurement via scaling or calibration, respectively. This linear relation can be presented graphically as a "sensitivity curve," or dose versus optical density plot. Each manufacturing batch of a given dosimeter may have its own sensitivity factor, or optical density change per unit of dose. Optical density ("OD") for radiochromic dosimeters can be defined as the logarithm of the ratio of incident light intensity to transmitted light:

$$\Delta OD = -\Delta \log_{10}\left(\frac{I_t}{I_0}\right). \quad (1)$$

Figure 3:
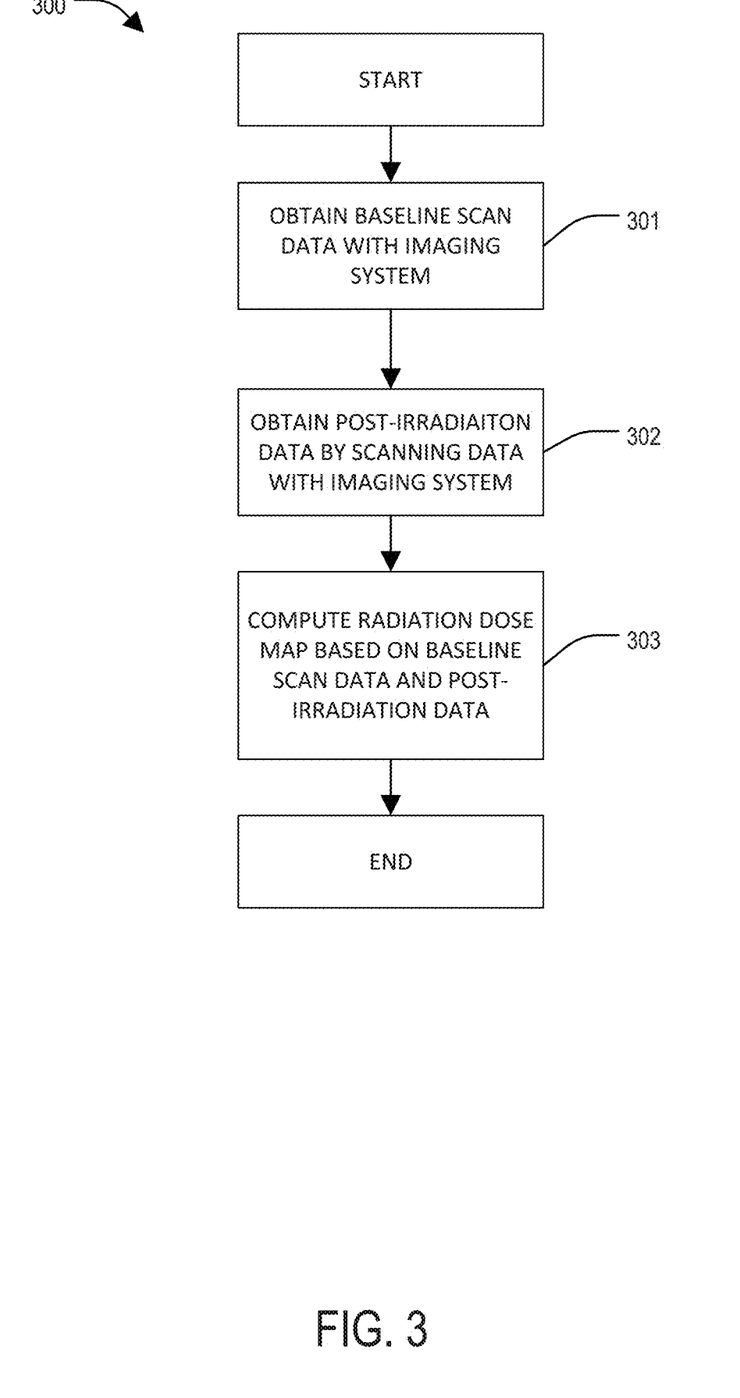
FIG. 3 depicts a method flowchart for providing a radiation dose chart in accordance with the teachings of the present disclosure.

FIG. 3 depicts a method flowchart 300 for providing a radiation dose map. The method includes obtaining baseline scan data by scanning the dosimeter using a measurement system before the dosimeter is exposed to the radiation 301. As an example, the baseline scan data can be acquired using an imaging system. The imaging system may be an optical computed tomography system. In such examples, the baseline scan data can include an optical density map that depicts a spatial distribution of optical density values measured in the dosimeter. Post-irradiation data are obtained by scanning the dosimeter using the measurement system after the dosimeter has been exposed to the radiation 302. The measurement system can be an imaging system. The imaging system can be an optical computed tomography system. In such examples, the post-irradiation data can be an optical density map that depicts a spatial distribution of optical density values measured in the dosimeter. Preferably, the same measurement system is used to obtain both the baseline scan data and the post-irradiation scan data, such that variations between the baseline scan data and the post-irradiation data that may arise from different measurement system settings can be minimized. A radiation dose map is then computed based on the baseline scan data and the post-irradiation data 303. As one example, the radiation dose map can be computed based on a difference between the baseline scan data and the post-irradiation data. For instance, an optical density change map can be generated by computing the difference between a baseline scan optical density map and a post-irradiation optical density map. Such a change in optical density map depicts a spatial distribution of the change in optical density values in the dosimeter caused by irradiating the dosimeter. From this change in optical density map, a radiation dose map can be generated, where the radiation dose map depicts a spatial distribution of radiation dose imparted to the dosimeter. In some other embodiments, the radiation dose map can itself include the change in optical density map.

The baseline scan data and the post irradiation data may both be obtained and provided to the computer system using the same imaging system. The baseline scan data and the post irradiation data may be obtained by scanning the dosimeter using an optical imaging system. The optical imaging system may be an optical computed tomography system. If such an optical-CT system is used, the computed temporal correction factor may indicate a change in an optical characteristic of the dosimeter between the first time point and the second time point. The optical characteristic may be coloration or optical density. The radiation dose map may be a three-dimensional radiation dose map that depicts a spatial distribution of radiation dose imparted to the dosimeter, wherein the pixel values in the radiation dose map are voxel values.

One example of an imaging system that can be used to obtain and provide the baseline scan data and the radiation dose map is the Duke Large FOV Optical-CT Scanner (DLOS). The DLOS imaging system is bi-telecentric, including a matched light source and imaging lens, each with a 24 cm FOV. Light emitted from the LED source is subject to a 632 nm/10 nm bandwidth filter and 120-grade diffuser, prior to entering the light-source lens. The parallel beam of light rays pass through an oil bath containing the dosimeter and are then imaged with a camera. The dosimeter is fixed to a rotating stage within the tank, projections at fixed degree increments are acquired with each projection being the result of multiple averaged images to reduce noise introduced by the detector. When acquiring the radiation dose map, the dosimeter may be scanned with the same FOV and acquisition parameters. The dosimeter used to obtain the baseline scan may be a different dosimeter than the dosimeter from which the radiation dose map is obtained.

As another example, the optical imaging system can be an optical computed tomography system that implements a dry-tank, such as the one described in co-pending U.S. patent application Ser. No. 15/941,149, which is herein incorporated by reference in its entirety.

The dosimeter may be transported from the first location to the second location where it may undergo irradiation at a first time point. Radiation may be imparted to the dosimeter by a radiation therapy system. Example of radiation therapy systems include an intensity modulated radiotherapy (IMRT) system, an image guided radiotherapy (IGRT) system, stereotactic body radiotherapy systems, or similar system known in the art. The dosimeter may be specifically exposed to radiation via a magnetic resonance imaging-guided radiotherapy system.

After irradiation, the dosimeter may be transported from the second location to the first location where the dosimeter may be scanned to obtain the radiation dose map at a second time point. The amount of time between the first time point and the second time point may be less than 168, 72, 48, 36, 24, 12, 6, 4, 2, 1, or 0.5 hours. This amount of time may be specifically less than 48 hours. This amount of time may be specifically less than 24 hours. Between the first time point and the second time point, the temperature of the dosimeter may be maintained between within a range of temperatures. As one example, the range may be 20 to 25 degrees Celsius. In other examples, the temperature of the dosimeter can be allowed to fluctuate in a broader range. The temperature of the dosimeter may also be maintained between the range of temperatures (e.g., between 20 and 25 degrees Celsius) from the time it is shipped from the first location to the second location (e.g., before the first time point), and the time it is received back at the first location (e.g., the second time point). If temperatures significantly deviate from a standard room temperature of 23 degrees Celsius, the temporal and spatial correction factors may not accurately compensate for inaccuracies. In such instances, the temporal and spatial correction factors may need to be adjusted based on the temperature changes experienced by the dosimeter.

Processing of the radiation dose map and the baseline scan as well as generation of the corrected radiation dose map may be performed on a computer system. The computer system may be electrically connected to the imaging system. The computer system may allow for additional information to be submitted by a user during processing and generation. The user may input various information into the computer system. For example, the user may input various information into a Matlab-based graphical user interface (GUI) reconstruction program. Examples of information to be inputted include the size, shape, identifier, and composition of the dosimeter to the computer system. Additionally, information regarding the intended radiation dose applied to the dosimeter may be transferred from the radiotherapy system to the computer system. For example, the radiation treatment plan may be exported in DICOMRT format from the treatment planning software (TPS) into the computer system for processing.

The radiation dose map data can be modified into a dose measurement using a multitude of methods including: (1) scaling to a high-dose region of the verification plan as a reference or (2) to a reference point where an absolute dose measurement was taken. Further, when calculating the appropriate delivered dose using an optical-CT system, factors such as path length (e.g., dosimeter diameter), dynamic range (e.g., pre-scan counts), and batch sensitivity (e.g., as estimated by cuvette calibration) may be used in the calculation. To quantify radiation induced change in optical density ($\Delta OD$), the baseline scan data may be compared with optical density measurements made at the second time point. Although the present disclosure may determine the spatial and temporal correction factors using $\Delta OD$, one of skill in the art could readily envision using a similar metric of comparison during processing of the empirical data.

The spatial and temporal correction factors may be derived from the empirical data. Further information about the size, shape, or composition of the dosimeter may also be provided to the computer system. For example, the diameter of the dosimeter may be provided to the computer system. The temporal correction factor may be calculated by providing a reference radiation dose map to the computer system and computing the temporal correction factor using the radiation dose map and the reference radiation dose map. The reference radiation dose map may be taken at a reference time point ($t_i$) and the radiation dose map may be imaged at second time point ($t_f$). The reference time point may occur between the first time point and the second time point.

The reference radiation dose map may be obtained by measuring radiation dose imparted to a second dosimeter that is similar to the dosimeter from which the radiation dose map was obtained (e.g., when obtaining a single reference radiation dose map from a different reference dosimeter, which is then used to compute a temporal correction factor for a second dosimeter using a radiation dose map obtained from that second dosimeter). Alternatively, the reference radiation dose map may be obtained by measuring the radiation dose map from the same dosimeter (e.g., when pre-computing a temporal correction factor for later use with different dosimeters).

The temporal correction factor may be computed as a ratio between the radiation dose map and the reference radiation dose map. For example, the temporal correction factor ($C_T$) may be calculated using an analytical fit, or via Equation 2:

$$C_T = \frac{\Delta OD_{t=t_i}}{\Delta OD_{t=t_f}} \qquad (2)$$

The spatial correction factor ($C_R$) may be derived from the empirical data. The spatial correction factor may be calculated by providing a reference radiation dose map to the computer system and computing the spatial correction factor using the radiation dose map and the reference radiation dose map. The reference radiation dose map may be the same reference dose map used in the calculation of the temporal correction factor. The spatial correction factor may be computed by first generating a dose cube by computing a difference between the radiation dose map and the reference radiation dose map. For example, the change in optical density at the second time point may be subtracted from the first time point, as in Equation 3:

$$\Delta OD_{rad} = \Delta OD_{t=t_f} - \Delta OD_{t=t_i} \qquad (3)$$

The resulting values ($\Delta OD_{rad}$) can then be spatially compared to obtain the spatial correction factor. Specifically, the spatial correction factor may be computed by normalizing a radiation dose value in the dose cube associated with a spatial location in the dosimeter with a radiation dose value in the dose cube associated with a center of the dosimeter. For example, if the dosimeter is cylindrical and being examined in a radial spatial dimension, the $\Delta OD_{rad}$ values at a given location ($r=r'$) may be normalized to the center of the dosimeter ($r=0$), as in Equation 4:

$$C_R = \frac{\Delta OD_{rad}(r = r')}{\Delta OD_{rad}(r = 0)} \qquad (4)$$

Data for temporal and spatial corrections, $C_T$ and $C_R$, may be further analyzed to determine applicable functions. For example, the data may be imported into a computational software (e.g. MATLAB) for curve-fitting to a best-fit model, outputting applicable polynomial functions.

Once the temporal and spatial correction factors have been computed, the corrected radiation dose map may be generated by the computer system. The correction factors may be used along with the radiation dose map data to produce the corrected dose map representative of a dose map that occurs at an earlier point in time (e.g., the first time point). Generating the corrected radiation dose map may include multiplying the radiation dose map by the temporal correction factor before subtracting the spatial correction factor. One exemplary equation for calculating the corrected ΔOD of the dose map is provided in equation 5:

$$\Delta OD_{t=t_i} = \Delta OD_{t=t_f} \times C_T(t) - C_R(r) \quad (5)$$

Application of equation 6 allows for the correction of each element within a scan taken at $t=t_f$ back to $t=t_i$, as well as further extrapolation. This example equation for correcting for temporal and spatial effects assumes ΔOD response-linearity at t=1 hr and relative inter-batch consistency of these effects. Other models that relax these assumptions while still implementing the temporal and spatial correction factors can be used.

Figure 4:
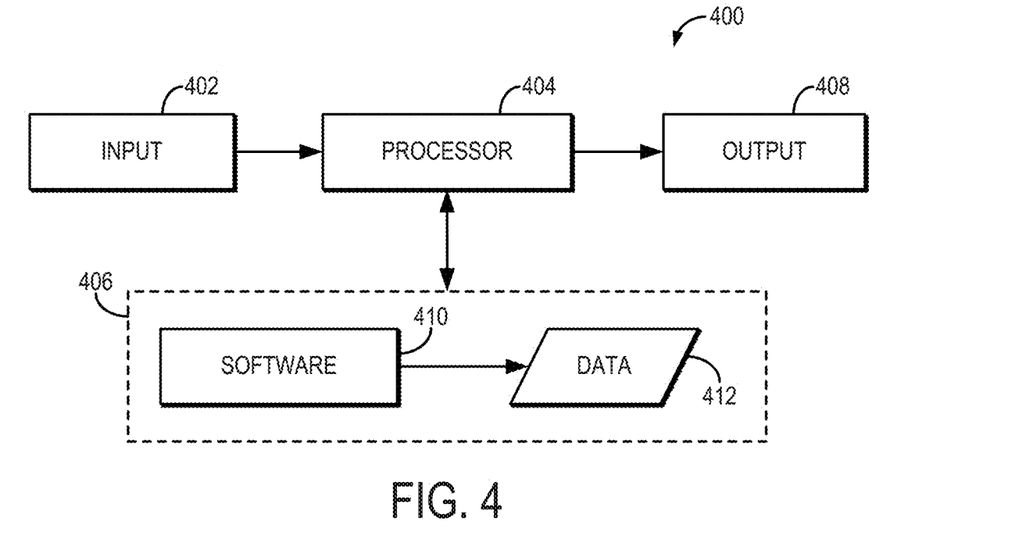
FIG. 4 is a block diagram of an example computer system that can implement the methods described in the present disclosure.

Referring now to FIG. 4, a block diagram of an example of a computer system 400 that can perform the methods described in the present disclosure is shown. The computer system 400 generally includes an input 402, at least one hardware processor 404, a memory 406, and an output 408. Thus, the computer system 400 is generally implemented with a hardware processor 404 and a memory 406.

In some embodiments, the computer system 400 can be a workstation, a notebook computer, a tablet device, a mobile device, a multimedia device, a network server, a mainframe, one or more controllers, one or more microcontrollers, or any other general-purpose or application-specific computing device.

The computer system 400 may operate autonomously or semi-autonomously, or may read executable software instructions from the memory 406 or a computer-readable medium (e.g., a hard drive, a CD-ROM, flash memory), or may receive instructions via the input 402 from a user, or any another source logically connected to a computer or device, such as another networked computer or server. Thus, in some embodiments, the computer system 400 can also include any suitable device for reading computer-readable storage media.

In general, the computer system 400 is programmed or otherwise configured to implement the methods and algorithms described in the present disclosure. For instance, the computer system 400 can be programmed to compute radiation dose maps based on data measured from a radiation dosimeter; compute temporal and spatial correction factors as described in the present disclosure; generate corrected radiation dose maps using the temporal correction factors, spatial correction factors, or both; and other suitable calculations that may be useful when implementing the methods described in the present disclosure.

The input 402 may take any suitable shape or form, as desired, for operation of the computer system 400, including the ability for selecting, entering, or otherwise specifying parameters consistent with performing tasks, processing data, or operating the computer system 400. In some aspects, the input 402 may be configured to receive data, such as data acquired with a measurement system, which may be an imaging system such as an optical computed tomography system. Such data may be processed as described above to compute temporal correction factors, spatial correction factors, or both, as well as to generate corrected radiation dose maps using such correction factors. In addition, the input 402 may also be configured to receive any other data or information considered useful for generating corrected radiation dose maps using the methods described above.

Among the processing tasks for operating the computer system 400, the one or more hardware processors 404 may also be configured to carry out any number of post-processing steps on data received by way of the input 402.

The memory 406 may contain software 410 and data 412, such as data acquired with a measurement system (e.g., an optical computed tomography system, other imaging system, or other suitable radiation measurement system), and may be configured for storage and retrieval of processed information, instructions, and data to be processed by the one or more hardware processors 404. In some aspects, the software 410 may contain instructions directed to computing radiation dose maps based on data measured from a radiation dosimeter; computing temporal and spatial correction factors as described in the present disclosure; generating corrected radiation dose maps using the temporal correction factors, spatial correction factors, or both; and performing other suitable calculations that may be useful when implementing the methods described in the present disclosure.

In addition, the output 408 may take any shape or form, as desired, and may be configured for displaying radiation dose maps, corrected radiation dose maps, optical density maps, and change in optical density maps, in addition to other desired information.

EXAMPLES

The following Examples are provided in order to demonstrate and further illustrate certain embodiments and aspects of the present disclosure and are not to be construed as limiting the scope of the disclosure.

Example 1

A detailed study of PRESAGE® dosimeters (2 kg) was conducted to investigate the temporal and spatial stability of radiation induced optical density change (ΔOD) over 8 days. Temporal stability was investigated on 3 dosimeters irradiated with four equally-spaced square 6 MV fields delivering doses between 10 cGy and 300 cGy. Doses were imaged (read-out) by optical-CT at multiple intervals. Spatial stability of ΔOD response was investigated on 3 other dosimeters irradiated uniformly with 15 MV extended-SSD fields with doses of 15 cGy, 30 cGy and 60 cGy. Temporal and spatial (radial) changes were investigated using CERR and MATLAB's Curve Fitting Tool-box. A protocol was developed to extrapolate measured ΔOD readings at t=48 hr (a typical shipment time in remote dosimetry) to time t=1 hr.

Although remote dosimetry has been demonstrated in the prior work, in this example study a new formulation in a larger volume (2 kg) in preparation for off-site deliveries on an MR-IGRT system was characterized. Both small volume (4 ml cuvette) and large volume (1 kg & 2 kg) studies of PRESAGE were conducted to investigate temporal and spatial behaviors over time.

Figure 5:
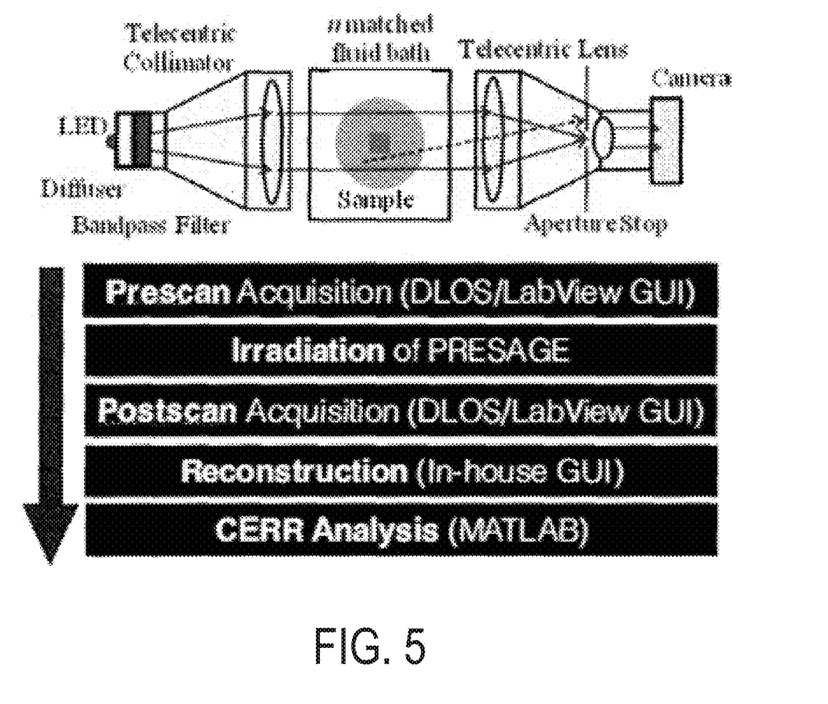
FIG. 5 depicts a schematic of the imaging system and process used to acquire baseline image data and radiation dose maps in the experimental study of Example 1.

FIG. 5 depicts a schematic of the imaging system and process used to acquire baseline image data and radiation dose maps in the experimental study. Baseline scans of 5×2 kg dosimeters were acquired at Duke, shipped to WashU for delivery of recommended TG-119 plans on the ViewRay, and subsequently shipped back for post-scan and analysis. Temporal and spatial effects modeled during formulation characterization were modeled in the form of corrections, ultimately to establish a refined 3D remote dosimetry protocol. The refined remote dosimetry protocol (including polynomial correction terms for temporal and spatial effects, $C_T$ and $C_R$) was then applied to the independent dosimeters irradiated with MR-IGRT treatments.

Throughout the study, all PRESAGE® dosimeters were maintained at room temperature (T=23° C.). PRESAGE® dose-response sensitivity studies were performed in 4 ml cuvettes to verify linearity, MR-compatibility, and energy-independence in remote dosimetry use. Pre-measurements of two sets of six cuvettes were taken at Duke, shipped to WashU for irradiation on a LINAC (6 MV) and MRIdian® ($E_{eff}$=1.25 MV) at 600M U/min to known doses (0, 2.5, 5.0, and 10.0 Gy) at 100 cm SSD, 5.5 cm depth in solid water, and then subsequently sent back to Duke for post-measurements. Absorption readings were taken with a Spectronic Genesys 20 spectrophotometer (Thermo Electron Scientific Instruments Corp., Madison, Wis.) at 633 nm, the peak absorption wavelength of LMG. Change in optical density was calculated by subtracting the pre- and post-irradiation absorption values.

Using 1 kg PRESAGE®, an open calibration field (6.5 Gy prescription) was delivered on the MRIdian® to examine the percent depth dose and a symmetrical 3-field plan (9.0 Gy prescription) with three adjacent regions of varying dose to determine uniformity within the dosimeter under a magnetic field. In both cases, dosimeters were positioned on the table on a support structure without a bolus.

The appropriate delivered dose should be calculated to avoid saturation (over-darkening) during optical-CT readout, while also maximizing signal-to-noise ratio (SNR). Previous dose calculation methods assumed uniformly delivered dose distribution, serving as a satisfactory approximation to avoid saturation. Through the analysis of the treatment plan in CERR prior to irradiation, the Dosimeter Dose Calculator (DDC), developed in-house at Duke University, affords a better estimation of the appropriate prescription dose, making full use of the dynamic range of the 12-bit CCD in the PRESAGE®/optical-CT system. Factors such as path length (dosimeter diameter), dynamic range (pre-scan counts), and batch sensitivity (best estimated by cuvette calibration) were used in the calculation.

A detailed study of PRESAGE® dosimeters (2 kg) was conducted to investigate the temporal and spatial stability of radiation induced optical density change ($\Delta$OD) over one week. Temporal and spatial (radial) changes were investigated using CERR and MATLAB's Curve Fitting Tool-box. A protocol was developed to extrapolate measured $\Delta$OD readings at t=48 hr (the typical shipment time in remote dosimetry) to time t=1 hr.

Retention of response linearity was investigated on 3 dosimeters irradiated with four equally-spaced square 6 MV fields delivering doses between 10 cGy and 300 cGy. These doses were chosen based on the delivered MR-IGRT plans later in the study. Doses were imaged (read-out) by optical-CT at multiple intervals and tracked for several days, post-irradiation, to mimic a remote dosimetry study (time points, t=1 hr, t=24 hrs, t=48 hrs, t=72 hrs, t=96 hrs, and t=192 hrs). For comparison, small volume temporal stabilities were conducted concurrently by irradiating on a 6 MV linac at 600 MU/min at doses of 0, 2.5, 5.0, and 10 Gy, following the irradiation and scanning protocol discussed above.

After completion of temporal and spatial studies, data were compiled, modeled and plotted. The temporal correction for scan-time t=48 hrs, $C_T$, was derived from the empirical data. The calculation for $C_T$ involved the division of the registered $\Delta$OD cubes at t=1 hr and t=48 hr, shown in equation 6 below:

$$C_T = \frac{\Delta OD_{t=1hr}}{\Delta OD_{t=48hrs}} \qquad (6)$$

Derivation of the spatial correction for scan-time t=48 hrs ($C_T$) involved the subtraction of registration $\Delta$OD cubes for time-stamp t=1 hr from t=48 hrs, as displayed below:

$$\Delta OD_{rad} = \Delta OD_{t=48\ hrs} = -\Delta OD_{t=1\ hr} \qquad (7)$$

The resultant dose cube ($\Delta OD_{rad}$) was normalized by the value located at the dosimeters center:

$$C_R = \frac{\Delta OD_{rad}(r=r')}{\Delta OD_{rad}(r=0)} \qquad (8)$$

Data for temporal and spatial corrections, $C_T$ and $C_R$, were imported into MATLAB's curve-fitting for a best-fit model, outputting applicable polynomial functions. Finally, the equation for corrected $\Delta$OD containing both a temporal and spatial correction term is displayed below:

$$\Delta OD_{t=1\ hr} = \Delta OD_{t=48\ hrs} \times C_T(t) - C_R(r) \qquad (9)$$

Application of equation 9 involved correcting each element within a scan taken at t=48 hr back to t=1 hr. This method of correcting for temporal and spatial effects assumed $\Delta$OD response-linearity at t=1 hr and relative inter-batch consistency of these effects.

After initial formulation characterization and remote dosimetry protocol refinement, TG-119 plans were created in the MRIdian®'s TPS and analyzed using the DDC to determine an appropriate prescription dose, described above. The TG119 recommended plans delivered to 5×2 kg PRESAGE® dosimeters were as follows: Multi-target, Prostate, H&N, C-Shape, and APPA. Dose readout was performed upon arrival at Duke (t=48 hr), post-irradiation, using the protocol discussed above. Temperature was tracked using Track-it data logger (Monarch Instruments, Amherst, N.H.) to confirm whether dosimeters were successfully maintained at room temperature throughout initial and return shipment. Absolute dose was measured using an IBA CC01 ion chamber in a 2 kg PRESAGE phantom with an ion chamber channel. Observed temporal and spatial effects modeled in the form of correction were applied to the TG119 remote dosimetry data, to correct back to time-stamp, t=1 hr, when dose-response linearity.

All dosimeters were observed to gradually darken with time (<5% per day). Consistent intra-batch sensitivity (0.0930±0.002 $\Delta$OD/cm/Gy) and linearity ($R^2$=0.9996) was observed at t=1 hr. A small radial effect (<3%) was observed, attributed to curing thermodynamics during manufacture. The refined remote dosimetry protocol (including polynomial correction terms for temporal and spatial effects, CT and CR) was then applied to independent dosimeters irradiated with MR-IGRT treatments. Excellent line profile agreement and 3D-gamma results for 3%/3 mm, 10% threshold were observed, with an average passing rate 96.5%±3.43%.

The methods described in the present disclosure advantageously provide for the identification, quantification and modeling of temporal and spatial effects observed in PRESAGE® and other similar dosimeters over time. As previously stated, all dosimeters were observed to gradually darken with time, less than 5% per day, with a small radial dependence of less than 3%. These physical changes can be attributed to curing thermodynamics during manufacture (exothermic setting of dosimeters).

The present disclosure has described one or more preferred embodiments, and it should be appreciated that many equivalents, alternatives, variations, and modifications, aside from those expressly stated, are possible and within the scope of the invention.

The invention claimed is:

1. A method for generating a radiation dose map of a dosimeter indicating a spatial distribution of radiation dose imparted to the dosimeter, the steps of the method comprising:
   (a) providing to a computer system, a radiation dose map obtained by measuring radiation dose imparted to a dosimeter after the dosimeter was exposed to radiation;
   (b) providing to the computer system, a temporal correction factor that indicates a change in a measure of radiation dose imparted to the dosimeter between a first time point when the dosimeter was exposed to the radiation and a second time point when the radiation dose map was obtained;
   (c) providing to the computer system, a spatial correction factor that indicates a sensitivity of the dosimeter to radiation measurements as a function of a spatial dimension; and
   (d) generating a corrected radiation dose map with the computer system by applying the temporal correction factor and the spatial correction factor to the radiation dose map, the corrected radiation dose map having pixel values associated with the measured radiation dose having been corrected for temporal effects caused by changes in the measure of radiation dose imparted to the dosimeter between the first time point and the second time point, and for spatial effects caused by the sensitivity of the dosimeter to radiation measurements as a function of the spatial dimension.

2. The method as recited in claim 1, wherein providing the temporal correction factor to the computer system includes providing a reference radiation dose map to the computer system and computing the temporal correction factor using the radiation dose map and the reference radiation dose map.

3. The method as recited in claim 2, wherein the temporal correction factor is computed as one of an analytical fit or a ratio between the radiation dose map and the reference radiation dose map.

4. The method as recited in claim 2, wherein the reference radiation dose map is obtained by measuring radiation dose imparted to a second dosimeter that is similar to the dosimeter from which the radiation dose map was obtained.

5. The method as recited in claim 1, wherein providing the spatial correction factor to the computer system includes providing a reference radiation dose map to the computer system and computing the spatial correction factor using the radiation dose map and the reference radiation dose map.

6. The method as recited in claim 5, wherein computing the spatial correction factor comprises:
   generating a dose cube by computing a difference between the radiation dose map and the reference radiation dose map; and
   computing the spatial correction factor by normalizing a radiation dose value in the dose cube associated with a spatial location in the dosimeter with a radiation dose value in the dose cube associated with a center of the dosimeter.

7. The method as recited in claim 1, wherein generating the corrected radiation dose map includes multiplying the radiation dose map by the temporal correction factor before subtracting the spatial correction factor.

8. The method as recited in claim 1, wherein the radiation dose map is a three-dimensional radiation dose map that depicts a spatial distribution of radiation dose imparted to the dosimeter, and wherein the pixel values in the radiation dose map are voxel values.

9. The method as recited in claim 1, wherein the spatial dimension is a radial dimension.

10. The method as recited in claim 1, wherein providing the radiation dose map comprises:
    obtaining baseline scan data by scanning the dosimeter using an optical imaging system before the dosimeter is exposed to the radiation;
    obtaining post-irradiation data by scanning the dosimeter using the optical imaging system after the dosimeter is exposed to the radiation; and
    computing a difference between the baseline scan data and the post-irradiation data.

11. The method as recited in claim 10, wherein the optical imaging system is an optical computed tomography system.

12. The method as recited in claim 10, wherein the radiation dose map indicates a change in optical density in the dosimeter between the baseline scan data and the post-irradiation data, wherein the change in optical density is correlated with radiation dose imparted to the dosimeter.

13. The method as recited in claim 1, wherein the temporal correction factor indicates a change in an optical characteristic of the dosimeter between the first time point and the second time point.

14. The method as recited in claim 1, wherein the dosimeter is a radiochromic dosimeter composed of an optically transparent material.

15. The method as recited in claim 14, wherein the temporal correction factor indicates a change in an optical characteristic of the dosimeter between the first time point and the second time point.

16. The method as recited in claim 14, wherein the radiochromic dosimeter is composed of a material that is optically transparent at a range of wavelengths used to scan the dosimeter in order to obtain the radiation dose map.

17. The method as recited in claim 1, wherein a difference between the first time point and the second time point is less than 48 hours.

18. The method as recited in claim 17, wherein the difference between the first time point and the second time point is less than 24 hours.

19. The method as recited in claim 1, wherein the radiation dose imparted to the dosimeter is produced by a magnetic resonance imaging-guided radiotherapy system.

20. The method as recited in claim 1, wherein the temperature of the dosimeter is maintained between 20 and 25 degrees Celsius between the first time point and second time point.

* * * * *